United States Patent
Hollis et al.

(10) Patent No.: US 6,743,622 B2
(45) Date of Patent: *Jun. 1, 2004

(54) HOMOLOGOUS RECOMBINATION ANTIBODY EXPRESSION SYSTEM FOR MURINE CELLS

(75) Inventors: Gregory Franklin Hollis, Westfield, NJ (US); George E. Mark, Princeton Junction, NJ (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 421 days.

(21) Appl. No.: 08/744,685

(22) Filed: Nov. 7, 1996

(65) Prior Publication Data

US 2003/0124648 A1 Jul. 3, 2003

Related U.S. Application Data

(63) Continuation of application No. 08/439,400, filed on May 11, 1995, now abandoned, which is a continuation of application No. 08/173,800, filed on Dec. 23, 1993, now abandoned.

(51) Int. Cl.$^7$ ............................................. C12N 15/63
(52) U.S. Cl. .................................. 435/320.1; 536/23.5
(58) Field of Search ........................... 536/23.53, 23.5, 536/24.1; 435/91.1, 320.1

(56) References Cited

U.S. PATENT DOCUMENTS

| 5,204,244 A |   | 4/1993 | Fell et al. |
| 5,998,144 A | * | 12/1999 | Reff et al. |

FOREIGN PATENT DOCUMENTS

| EP | 0 315 062 |   | 10/1988 |
| WO | WO91/09955 |   | 11/1991 |
| WO | WO92/10561 |   | 6/1992 |
| WO | WO93/04169 |   | 4/1993 |
| WO | WO93/24642 |   | 9/1993 |
| WO | WO93/22443 |   | 11/1993 |
| WO | WO 95/17516 | * | 6/1995 |

OTHER PUBLICATIONS

Cruse et al., Illustrated Dictionary of Immunology, CRC Press, p. 159, 1995.*
Morrison et al., Ann. Rev. Immunol. 2:239–56, 1984.*
Paul, Fundamental Immunology, third edition, Raven Press, pp. 351–370, 1993.*
Dalente, Trends in Biotechnology, vol. 3, No. 9, 1985.*
Sambrook, J. et al., Expression of Cloned Genes in Cultured Mammalian Cells: Elements for Replication and Selection, Molecular Cloning, Second Edition, pps. 16.8–16.15, 1989.
DeMartino, J.A. et al., Rapid Humanization and Expression of Murine Monoclonal Antibodies, (1991), Antibody, Immunoconjugates, and Radiopharmaceuticals, 4, No. 4, pp. 829–835 (cumulative).
Fell, H.P. et al., Homologous recombination in hybridoma cells: Heavy chain chimeric antibody produced by gene targeting, (1989), Proc. Natl. Acad. Sci. USA, Immunology, 86, pp. 8507–8511 (cumulative).
Hasty, P. et al., The Length of Homology Required for Gene Targeting in Embryonic Stem Cells, (1991), Molecular and Cellular Biology, 11, No. 11, pp. 5586–5591 (cumulative).
Singer, I.I., Optimal Humanization of 1B4, an Anti–CD18 Murine Monoclonal Antibody, is Achieved by Correct Choice of Human V–Region Framework Sequences, (1993), The Jour. of Immunology, 150, pp. 2844–2857 (cumulative).
Yamawaki–Kataoka, Y. et al., Nucleotide sequences of gene segments encoding membrane domains of immunoglobulin γ chains, (1982), Proc. Natl. Acad. Sci. USA, Genetics, 79, pp. 2623–2627 (cumulative).
Hall B. and Milcarek, C., Sequence and Polyadenylation Site Determination of the Murine Immunoglobulin γ2a Membrane 3' Untranslated Region, (1989), Molecular Immunology, 26, No. 9, pp. 819–826 (cumulative).
Bebbington, C.R., et al., High–Level Expression of a Recombinant Antibody from Myeloma Cells Using a Glutamine Synthetase Gene as an Amplifiable Selectable Marker, (1992), Bio/Technology, 10, pp. 169–175 (cumulative).
Palladino, L.O. et al., A Method for Rapidly Assembling Complex Plasmid Constructs Without Propagation of Intermediates in *E. coli*, (1993), BioTechniques, 14, No. 5, pp. 754–755 (cumulative).
Yamawaki–Kataoka, Y. et al., The complete nucleotide sequence of mouse immunoglobulin γ2a gene and evolution of heavy chain genes: further evidence for intervening sequence–mediated domain transfer, (1981), Nucleic Acids Research, 9, pp. 1365–1381 (cumulative).

* cited by examiner

Primary Examiner—Larry R. Helms
(74) Attorney, Agent, or Firm—Sheldon O. Heber; Jack L. Tribble

(57) ABSTRACT

A specific locus in the genome of a murine host cell is identified which causes high levels of recombinant gene expression following stable integration, via homologous recombination, of the recombinant gene into the specific chromosomal locus. The selection of a favorable genome locus for the insertion and expression of a recombinant gene is disclosed, as are DNA vectors and host cells.

19 Claims, 6 Drawing Sheets

HOMOLOGOUS RECOMBINATION ANTIBODY EXPRESSION SYSTEM FOR MURINE CELLS

This is a continuation of U.S. Ser. No. 08/439,400, filed May 11, 1995, now abandoned, which is a continuation of U.S. Ser. No. 08/173,800, filed Dec. 23, 1993, now abandoned.

BACKGROUND

Recombinant expression constructs are routinely used to generate stable mammalian cell lines expressing a desired recombinant protein. These recombinant expression constructs may be of a type which remain as extrachromasomal plasmids in a transfected host cell, or may be a type which integrates into the genome of the host. Mammalian host cells which carry stably integrated copies of recombinant genes are typically more reliable with respect to maintenance and integrity of the recombinant gene. Once a recombinant mammalian host cell is identified which produces the recombinant protein, integrated copies of the recombinant gene may be more desirable to extrachromasomal copies of the gene.

However, the frequency of cell lines carrying stably integrated copies of a recombinant gene that express a desired recombinant protein at high levels is quite low. Typically, large numbers of stably transfected mammalian cells must be screened to identify clones which express the recombinant protein at high levels. This is widely believed to be due to the effects of the locus of insertion of the recombinant gene into the mammalian genome. Due to the size of the mammalian genome it is highly unlikely that a random integration event would result in the insertion of the recombinant gene into a locus favorable for high levels of gene expression.

An increase in the frequency of high level recombinant gene expressing cell lines would provide a much greater pool of high expressors to choose from for subsequent selection as the recombinant protein producer. In addition, the frequency increase would reduce the number of stable cell lines that would need to be generated to identify high level recombinant protein expressors.

SUMMARY OF THE DISCLOSURE

This invention discloses a method of defining a specific position in the mammalian genome that is favorable for high levels of recombinant gene expression and, an efficient method for increasing the frequency of high expressors by targeting the expression construct to a favorable genomic position.

Also disclosed is the operation of the method of this invention to establish a stable cell line expressing high levels of a recombinant protein. Further the invention shows that the cell line generated using this invention, expresses recombinant protein at extremely high levels, frequently exceeding the best expressing cell lines produced by random integration of the expression construct into the mammalian genome.

DETAILED DESCRIPTION OF THE INVENTION

Figure 1:
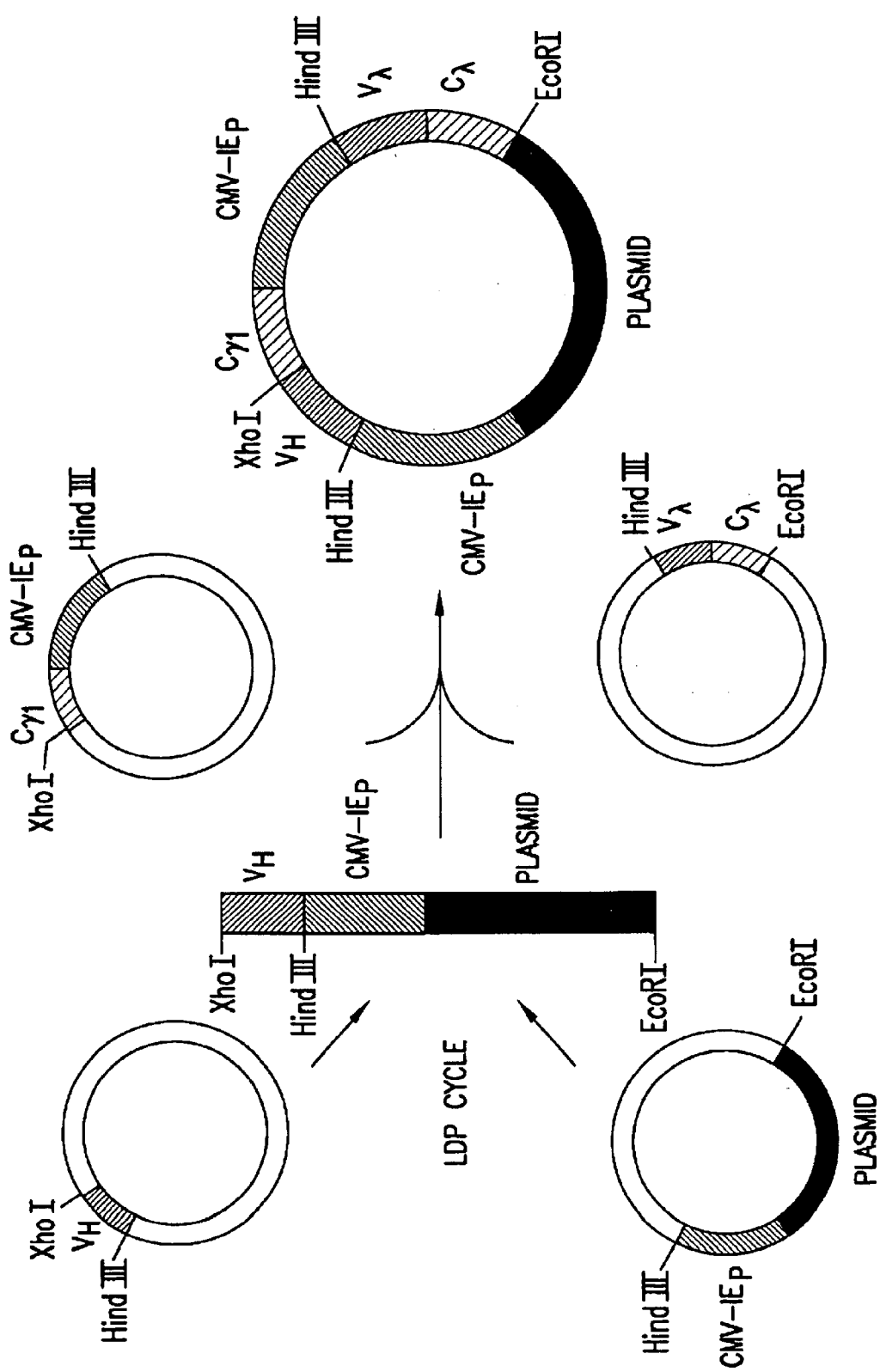
FIG. 1—A schematic diagram of plasmid p9014 is shown.

The present invention relates to a method of achieving high level expression of recombinant genes in mammalian cells. High levels of recombinant gene expression in the method of the present invention results from the site directed integration of recombinant genes into the host cell genome. The integration site is preselected, and the integration event is achieved through homologous recombination of a DNA vector containing specific DNA sequences known to be homologous with a specific site within the host genome. The specific site within the host genome is selected for insertion of the recombinant gene based on the determination that this site is highly active with respect to gene transcription and readily integrates homologous DNA segments.

Mammalian cells capable of being utilized in the method of the present invention include, but are not limited to, NS/0, cells and are the most preferred cells.

NS/0 cells (Galfre, G. and Milstein, C. Methods in Enzymology (1981), 73B, pp 3–46.) are grown in suspension at about 37° C. in, for example, Dulbecco's modified minimal essential medium (Hazelton Research Products) with about 10% fetal calf serum (HyClone; defined sera with no detectable endotoxin) or Iscove's Modified Dulbecco's Medium (JRH Biosciences) with about 9% horse serum. The cells are grown in roller bottles, Wheaton turbolift 46 liter suspension flasks (Wheaton), or 75, 200, or 300 liter fermenters with weekly harvests of about 1–2×106 cells/ml (3–4 doublings/week). Media for use in suspension flasks or fermenters may contain about 0.1–0.3% F68 pluronic to reduce shear force on the cells. Cells are typically grown for no more than 3–4 months following initial culturing.

Cell-free extracts are prepared from NS/0 cells by disruption of the cells by nitrogen cavitation, hypotonic lysis or the like. The cells are collected by centrifugation and may be washed in an isotonic buffer solution such as phosphate buffered saline, pH about 7.4. Hypotonic lysis is accomplished by washing the cells in about 10 volumes of hypotonic buffer (about 10 mM KCl, about 20 mM HEPES, about pH 7.4, about 1.5 mM $MgCl_2$, about 0.1 mM EDTA) or (about 25 mM HEPES, about pH 7.5, about 5 mM $MgCl_2$, and 1 mM EGTA) and collected by centrifugation. The lysis buffer may also contain a reducing agent such as dithiothreitol (DTT). The hypotonic buffer will generally contain protease inhibitors such as PMSF, leupeptin and pepstatin. The cells are resuspended in about 3 volumes of hypotonic buffer, placed on ice for about 20 min and lysed by about 20 strokes in a Dounce homogenizer. Disruption of about 90 to about 95% of the cells is obtained in a 100 or 300 ml tight filling Dounce homogenizer using about 25 or about 15 strokes respectively. Nitrogen pressure disruption also takes place in a hypotonic buffer. Resuspended cells are placed in a nitrogen pressure cell at 400 psi of nitrogen for about 30 min at about 4° C. with agitation. Disruption is accomplished by releasing the pressure and evacuating the cells from the pressure cell.

The cell lysate is clarified by successive centrifugation steps; at about 400 to about 1000×g (supernatant S1), at about 30,000×g (supernatant S2) and at about 300,000×g (supernatant S3). The cell lysate may also be clarified by the following procedure. Unbroken cells and nuclei are removed by centrifugation at about 3000 rpm, for about 10 minutes, at about 5° C. in a Beckman GPR centrifuge. The post nuclear supernatant fluid is centrifuged for about 20 minutes at about 16,000 rpm in a Sorval centrifuge with a SS34 rotor. The supernatant fluid is further clarified by centrifugation for about 60 minutes at about 50,000 rpm in a Beckman centrifuge (50.2Ti rotor) or 45,000 rpm (45Ti rotor). The resultant supernatant fluid is stored at about −80° C. following the addition of about 2 mM DTT and 0.1% CHAPS.

Any of a variety of procedures may be used to molecularly clone cDNA. These methods include, but are not limited to, direct functional expression of the recombinant gene following the construction of a cDNA library in an appropriate expression vector system. Another method is to screen a cDNA library constructed in a bacteriophage or plasmid shuttle vector with a labelled oligonucleotide probe designed from the amino acid sequence of the desired protein.

Preparation of cDNA libraries can be performed by standard techniques well known in the art. Well known cDNA library construction techniques can be found for example, in Maniatis, T., Fritsch, E. F., Sambrook, J., Molecular Cloning: A Laboratory Manual (Cold Spring Harbor Laboratory, Cold Spring Harbor, N.Y., 1982). It is readily apparent to those skilled in the art that DNA encoding the desired protein may also be isolated from a suitable genomic DNA library.

Construction of genomic DNA libraries can be performed by standard techniques well known in the art. Well known genomic DNA library construction techniques can be found in Maniatis, T., Fritsch, E. F., Sambrook, J. in Molecular Cloning: A Laboratory Manual (Cold Spring Harbor Laboratory, Cold Spring Harbor, N.Y., 1982).

In order to clone a recombinant gene by the preferred method, the amino acid sequence of the encoded protein may be necessary if no DNA sequence is available. To accomplish this, the desired protein may be purified and partial amino acid sequence determined by automated sequenators. It is not necessary to determine the entire amino acid sequence, but the linear sequence of one or more regions of about 6 to 8 amino acids determined for the PCR amplification of a partial DNA fragment.

Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the DNA sequence but will be capable of hybridizing to the DNA even in the presence of DNA oligonucleotides with mismatches. The mismatched DNA oligonucleotides may still sufficiently hybridize to the DNA to permit identification and isolation of DNA encoding the desired protein.

As used herein, all amino acid three letter and single letter designations conform to those designations which are standard in the art, and are listed as follows:

| Alanine | Ala | A |
| Arginine | Arg | R |

-continued

| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The cloned DNA obtained through the methods described above may be recombinantly expressed by molecular cloning into an expression vector containing a suitable promoter and other appropriate transcription regulatory elements, and transferred into prokaryotic or eukaryotic host cells to produce recombinant protein. Techniques for such manipulations are fully described in Maniatis, T, et al., supra, and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria, bluegreen algae, plant cells, insect cells and animal cells.

Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant proteins in mammalian cells. Commercially available mammalian expression vectors which may be suitable for recombinant protein expression, include but are not limited to, pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and IZD35 (ATCC 37565).

DNA encoding the desired protein may be cloned into an expression vector for expression in a recombinant host cell. Recombinant host cells may be prokaryotic or eukaryotic, including but not limited to bacteria, yeast, mammalian cells including but not limited to cell lines of human, bovine, porcine, monkey and rodent origin, and insect cells including but not limited to drosophila derived cell lines. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3

(ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

The expression vector may be introduced into host cells via any one of a number of techniques including but not limited to transformation, transfection, protoplast fusion, and electroporation. The expression vector-containing cells are clonally propagated and individually analyzed to determine whether they produce the recombinant protein. Identification of host cell clones expressing the recombinant protein may be done by several means, including but not limited to immunological reactivity with antibodies, and the presence of host cell-associated recombinant protein activity.

Following expression of the recombinant protein in a recombinant host cell, the protein may be recovered to provide the protein in purified form. Several purification procedures are available and suitable for use. Recombinant protein may be purified from cell lysates and extracts, or from conditioned culture medium, by various combinations of, or individual application of salt fractionation, ion exchange chromatography, size exclusion chromatography, hydroxylapatite adsorption chromatography and hydrophobic interaction chromatography.

In addition, recombinant proteins can be separated from other cellular proteins by use of an immuno-affinity column made with monoclonal or polyclonal antibodies specific for the recombinant protein. Antibodies are prepared according to methods well known in the art.

Monospecific antibodies are purified from mammalian antisera containing antibodies reactive against the recombinant protein or are prepared as monoclonal antibodies reactive with the recombinant protein using the technique of Kohler and Milstein, Nature 256: 495–497 (1975). Monospecific antibody as used herein is defined as a single antibody species or multiple antibody species with homogenous binding characteristics for the recombinant protein. Homogeneous binding as used herein refers to the ability of the antibody species to bind to a specific antigen or epitope, such as those associated with the recombinant protein, as described above. Specific antibodies are raised by immunizing animals such as mice, rats, guinea pigs, rabbits, goats, horses and the like, with rabbits being preferred, with an appropriate concentration of the recombinant protein either with or without an immune adjuvant.

The following procedures are preferred to prepare recombinant DNA sequences which incorporate the antibody variable regions, light chains and heavy chains obtained from human B cell lines combined with human constant regions. These recombinant DNAs can be used to transfect mammalian cells for the expression of a recombinant human antibody which retains the antigen specificity of the human-donor B cell-derived antibody. Preferably, the recombinant immunoglobulins will be recognized as self proteins when administered for therapeutic purposes. Total RNA is extracted from the human heterohybridomas, for example the human heterohybridoma cells described, using standard methods, for example involving cellular solubilization with guanidinium isothiocyanate (Chirgwin et al., Biochem. 18: 5294–5299 [1979]).

It is readily apparent to those skilled in the art that antibody producing cells are suitable for the preparation of recombinant DNA molecules encoding part or all of the antibody molecule. Such antibody producing cells include, but are not limited to those described in the ATCC Catalogue of Cell Lines And Hybridomas, 7th Edition, 1992. DNA encoding immunoglobulin heavy and light chains are disclosed and available sequence data for human antibody variable domains is complied by Kabat et al., "Sequences of Proteins of Immunological Interest", 4th ed., Bethesda, Md.: National Institutes of Health, 1987, updates to this database, and other accessible U.S. and foreign databases (both nucleic acid and protein sequences).

An expression plasmid, p9014 [Palladino et al., 1993, Biotechniques, 14, pp. 754–755] was constructed by standard DNA cloning methods, which contains the immunoglobulin heavy and light chain transcription units driven from the human cytomegalovirus immediate early promoters and uses the glutamine synthetase transcription unit as a selectable marker (FIG. 1). A cell line was generated by electroporating a Sal I linearized p9014 into the murine plasmacytoma cell line NS/0 and selecting for stable integrants by growth in glutamine free media [DeMartino et. al. Antibody, Immunoconjugates and Radiophannaceuticals 1991 4:829–835 and Singer et. al. Journal of Immunology 1993 150:2844–2857]. From the clones generated, D12 was selected for further study and was shown to express recombinant antibody at exceptionally high levels (>15 pg/cell/day). The high specific productivity of this clone suggests that the p9014 vector had inserted into the mouse genome at a privileged site for expression. As an initial step in characterizing the integration site of p9014 in these cells, genomic DNA was isolated from D12, digested with Xba I and probed with the human immunoglobulin kappa constant region fragment. Under stringent conditions, this fragment will only hybridize to the transfected gene and because it is present near the Sal I site used to linearize the plasmid, will identify the restriction fragment that contains the plasmid/mouse genomic DNA junction. This probe identified one 3.3 kb band in D12 genomic DNA representing one copy of integrated p9014. These results suggest that the high level of expression seen in the D12 clone are derived from a single copy of p9014 that inserted to produce a 3.3 kb Xba I junction fragment.

Figure 2:
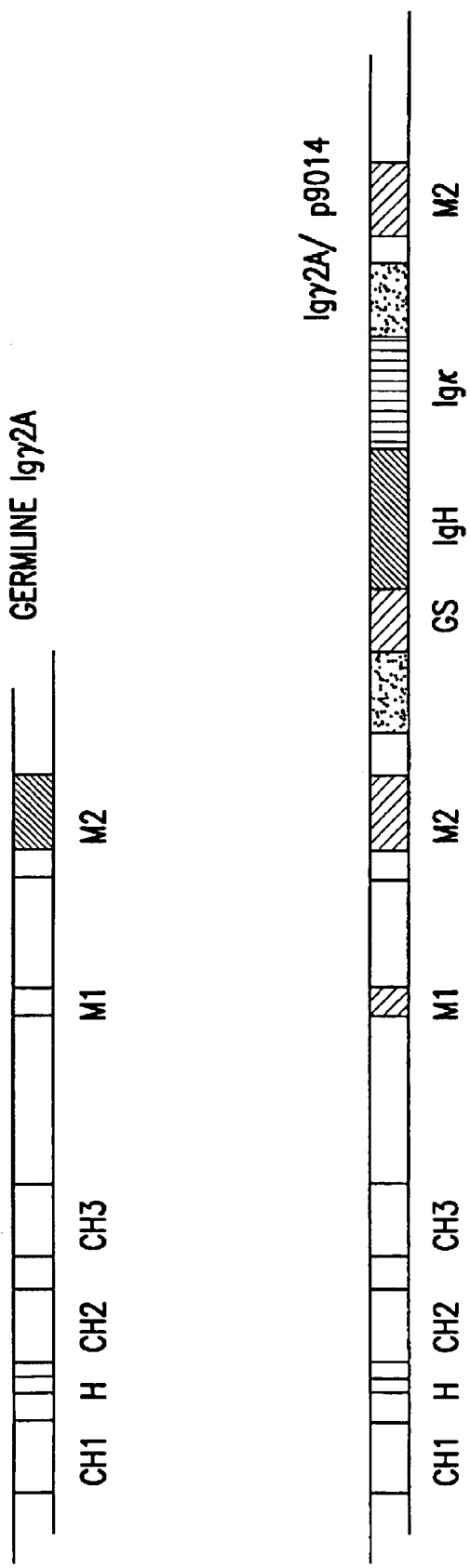
FIG. 2—The insertion site of p9014 into the mouse chromosome is shown.

To characterize this insertion site, total genomic D12 DNA libraries were made and recombinant bacteriophage plaques were screened with the human immunoglobulin kappa constant region probe and a plasmid probe from the other side of the Sal I site used to linearize the original plasmid prior to transfection. Recombinant bacteriophage clones containing p9014/murine genomic DNA junction fragments from both sides of the insertion site were isolated and subcloned into a plasmid. Sequence analysis of the murine genomic DNA at the position of integration demonstrated that the p9014 vector had inserted into the murine immunoglobulin gamma 2A locus. The insertion generated a 1.8 kilobase (kb) duplication of murine immunoglobulin gamma 2A gene beginning 48 base pair (b.p.) upstream of membrane exon 2 and extending downstream of the poly A addition signal. At the 3' plasmid/murine genomic DNA junction, 36 b.p. of DNA was present that was not derived from either the transfected vector or the murine immunoglobulin gamma 2A locus. At this junction, 32 b.p of plasmid sequence has been deleted. Examination of the 5' junction revealed that 791 b.p. of vector sequence was deleted in the insertion process and 16 b.p. of unidentified DNA was present (FIG. 2).

The original cell line used for the transfection, NS/0, is a fully differentiated B cell, a cell type that normally expresses extremely high levels of immunoglobulin RNA from the Ig heavy chain locus. The observation that p9014 inserted into this locus demonstrates that the CMV-IEp promoter, can be expressed at high levels in this chromosomal position. These results show that the use of homologous recombination to insert recombinant DNA expression vectors to this immunoglobulin locus may promote high levels of expression for other recombinant proteins in this cell line.

Figure 3A:
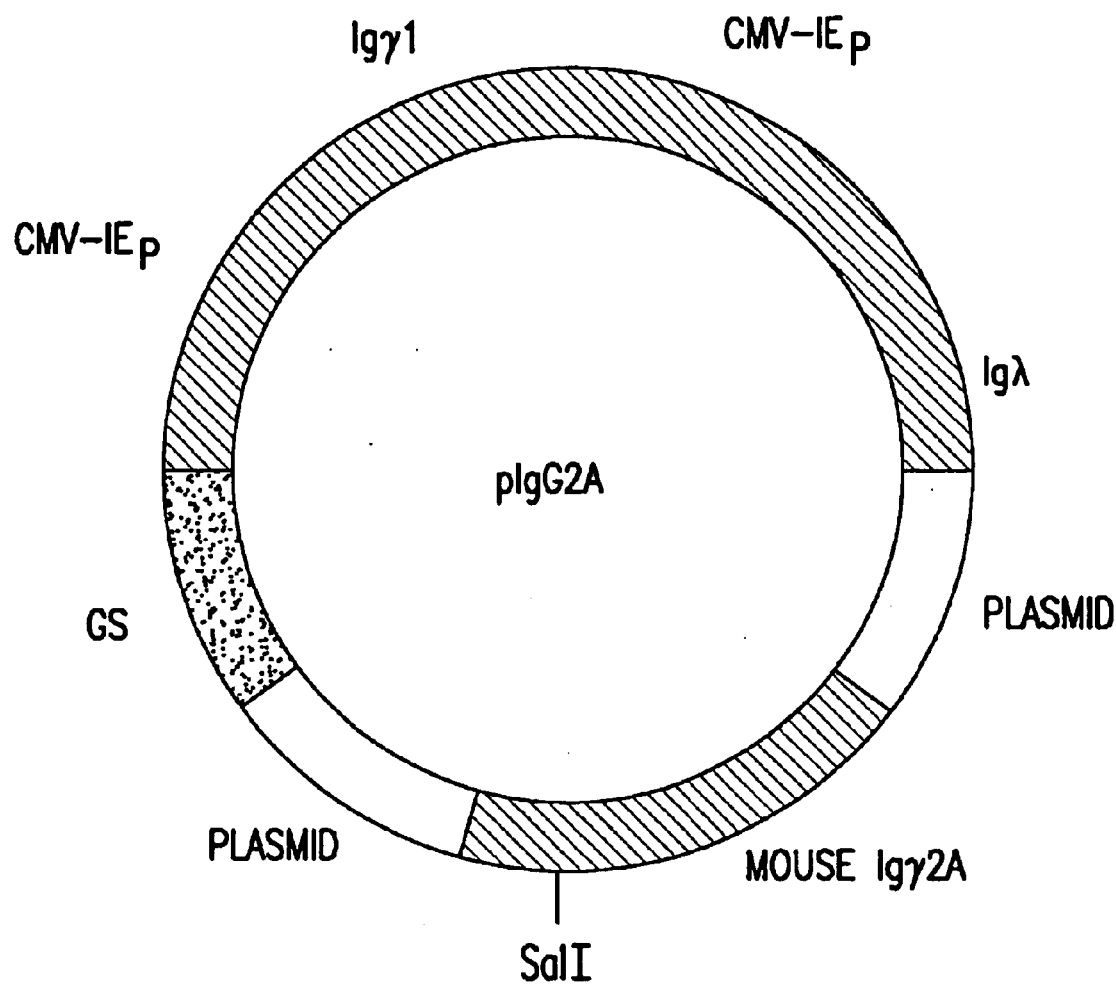
FIG. 3 panels A, B, and C—Panel A shows a diagram on the homologous recombination antibody expression plasmid pIgG2A; Panel B shows a diagram of the homologous recombination event for insertion of the antibody expression plasmid into the chromosome; and Panel C shows the portion of the chromosome containing the homologously recombined antibody expression plasmid.
Figure 3B:
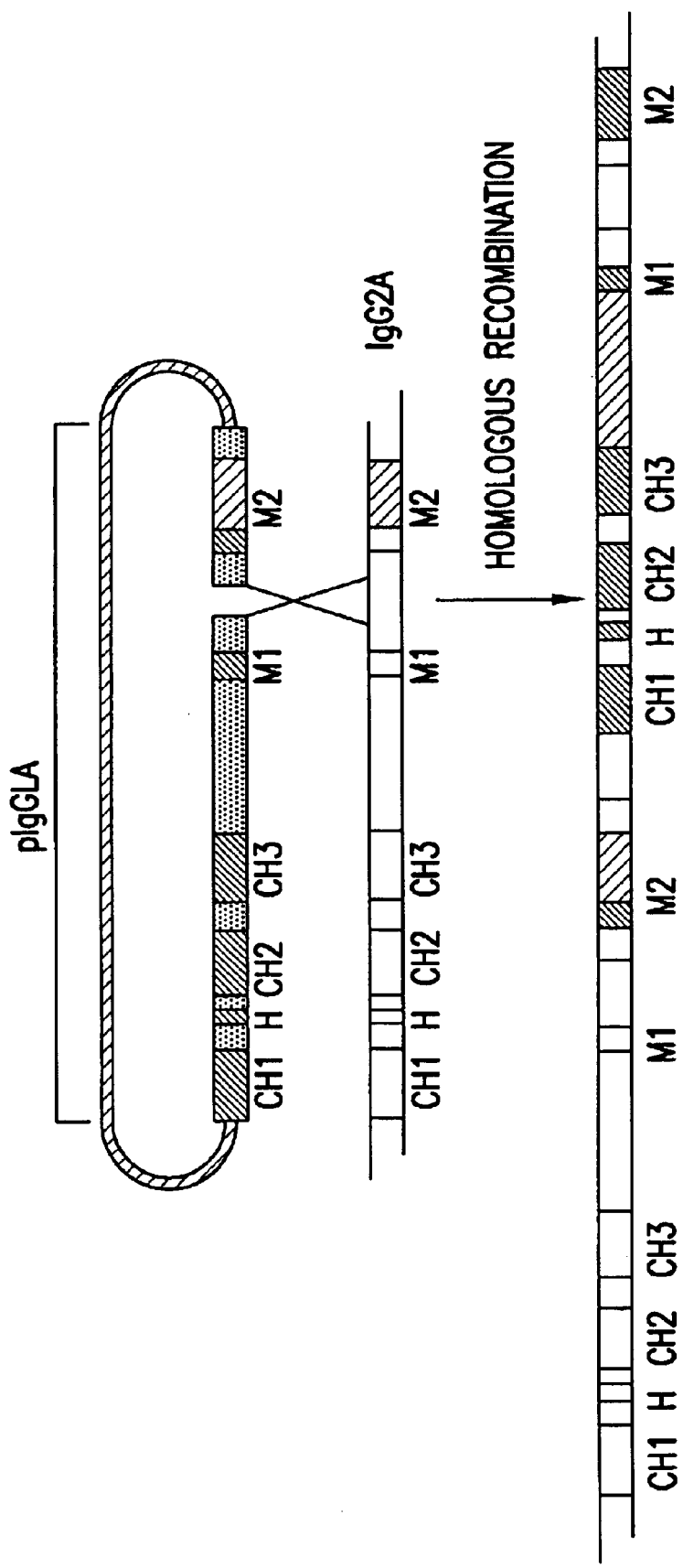

To evaluate this approach, an expression construct containing the germline murine immunoglobulin gamma 2A gene as a homologous recombination targeting sequence was generated. An NS/O genomic DNA bacteriophage library was made, screened with a probe from the M2 3' untranslated region of the murine IgG2A gene and several purified clones were shown to contain the entire germline murine IgG2A gene. From one of these bacteriophage, a 5.1 kb BamHI genomic fragment was subcloned which included all of the coding region of murine Ig gamma 2A except the most 5' part of the CH1 exon. A Sal I restriction site was inserted at the naturally occurring Stu I site present 39 b.p. upstream of membrane exon 2 to provide a unique site for linearization within the murine immunoglobulin gamma 2A sequence. This cloned fragment was used to generate a complex expression vector containing: 1) heavy and light chain immunoglobulin genes transcribed from a human CMV immediate early promoters; 2) a glutamine synthetase gene to be used as a selectable marker; 3) plasmid vector sequences; and 4) the 5.1 kb BamHI fragment of the murine immunoglobulin gamma 2A locus (FIG. 3A) [Yamawaki-Kataoka, Y. et. al. Proc. Natl. Acad. Sci. U.S.A. 1982 79:2623–2627; Hall, B. et. al. Molecular Immunology 1989 26:819–826, Yamawaki-Kataoka, Y. et. al. Nucleic Acid Research 1981 9:1365–1381; Bebbington, C. R. et. al. Biotechnology 1992 10:169–175]. This homologous recombination insertion type vector has been designed to optimize for integration events in which the murine immunoglobulin gamma 2A locus that is contained in the vector can recombine with the endogenous murine immunoglobulin gamma 2A locus causing a directed and defined insertion of the expression vector (FIG. 3B). It is expected that the insertion of this vector via homologous recombination at any site within the immunoglobulin gamma 2A locus will result in high level expression of the recombinant antibody-encoding DNA.

NS/O cells were transfected with the SalI linearized immunoglobulin vector construct by electroporation and were plated in 96 well microtiter plates. 147 wells were positive for cell growth under GS selective media conditions. Stable cell lines, which have integrated the immunoglobulin construct into the endogenous murine immunoglobulin gamma 2A locus by homologous recombination, express high levels of recombinant antibody. To rapidly screen for clones that were potential homologous recombinants, an ELISA was employed as a rapid first pass screen for wells expressing high levels of recombinant antibody. ELISA done on supernatants from all 147 wells identified 20 wells expressing high levels of the antibody. Cells from these 20 wells were expanded and reassayed for expression of antibody. Cells derived from 12 of the 20 wells continued to express high levels of antibody. These 12 cell lines formed the pool of clones that had inserted the pIgG2A/immunoglobulin plasmid into a chromosome.

Figure 3C:
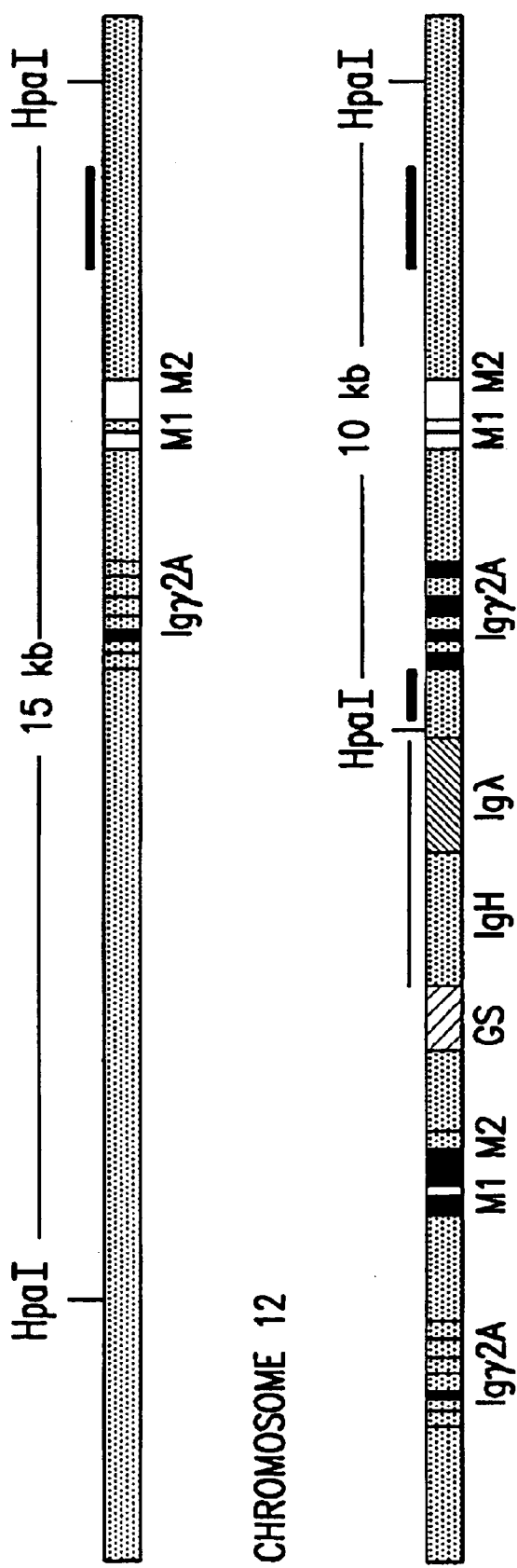

A genomic Southern blot assay was developed to identify stable clones in which the transfected vector had integrated into the murine immunoglobulin gamma 2A locus. A large number of restriction enzymes were scanned to identify a suitable enzyme for detecting homologous recombinants. HpaI gives a 15 kb germline band when NS/O genomic DNA is digested, blotted and probed with a murine immunoglobulin gamma 2A probe from the 3' side of the locus. In contrast, if the immunoglobulin vector has inserted into the IgG2A locus by homologous recombination, a 10 kb Hpa I fragment will be present on the blot (FIG. 3C).

Figure 4:
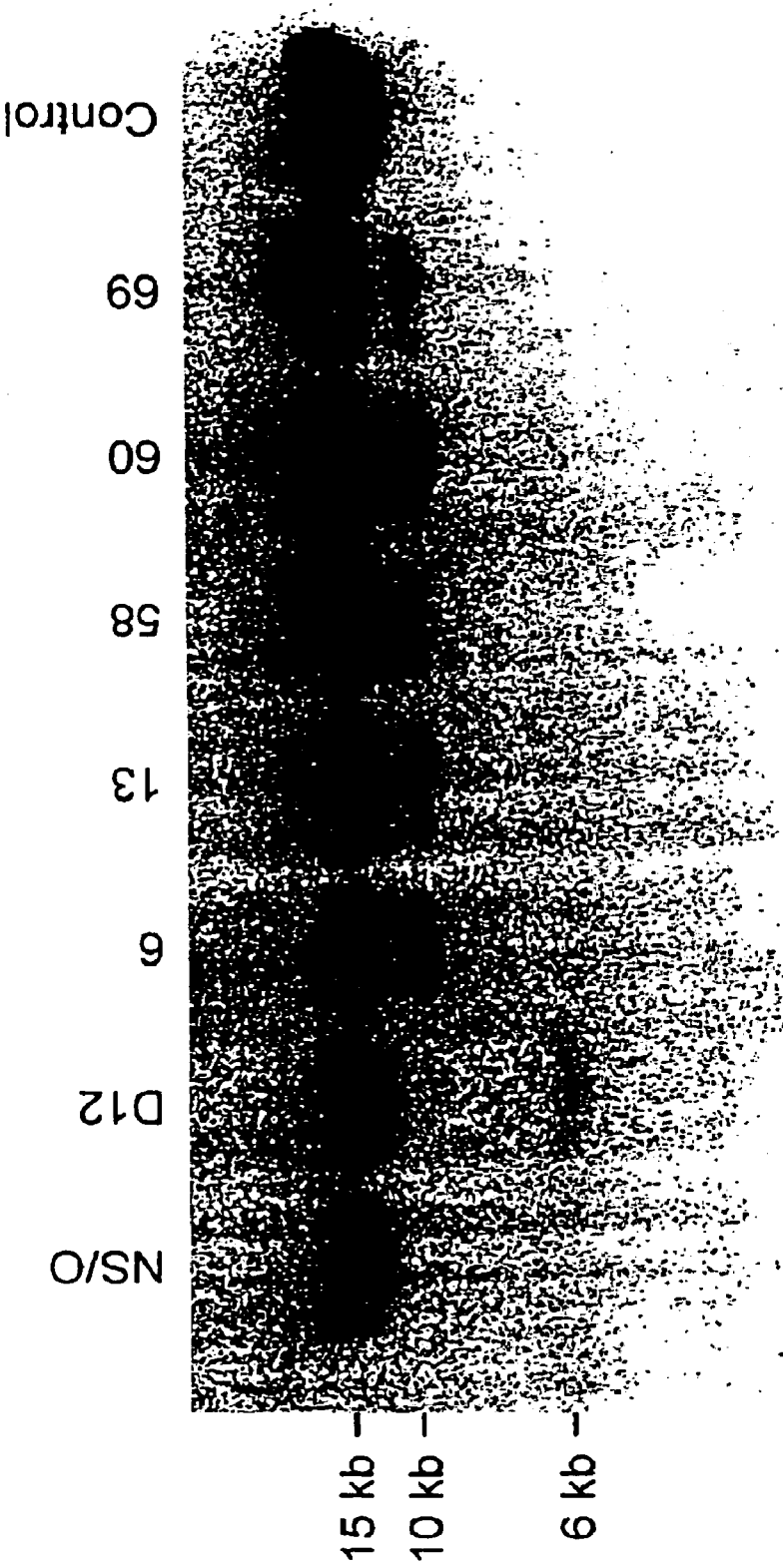
FIG. 4—A Southern blot analysis of the recombinant clones containing the homologously recombined antibody expression plasmid is shown.

Southern analysis of the 12 high expressing cell lines demonstrated that 9 of these cell lines had a 10 kb band consistent with the insertion of the construct into the murine IgG2A locus by homologous recombination. (Table 1 and FIG. 4). These 9 clones were confirmed to be homologous recombinants by additional Southern blots using a hybridization probe unique to the immunoglobulin expression vector. This result indicates that homologous recombination into the murine immunoglobulin gamma 2A locus occurred at an extremely high frequency. 75% of the high expressing clones and 6% of the total number of stable cell lines were homologous recombinants.

TABLE 1

| Clone no. | Homologous Recombinant | Specific Production pg/cell/day |
|---|---|---|
| 13 | Yes | 24.40 |
| 16 | Yes | 16.50 |
| 10 | Yes | 21.80 |
| 28 | No | 18.3 |
| 42 |  | 21.50 |
| 6 | Yes | 28.10 |
| 22 | No | 43.10 |
| 41 |  | 33.60 |
| 58 | Yes | 14.00 |
| 60 | Yes | 36.40 |
| 69 | Yes | 40.70 |
| 88 | No | 32.50 |

All 12 high expressing clones were examined for their level of recombinant protein productivity. Cell culture media was removed from cells plated at known density at 24, 48 and 72 hours and Poros assays were run to determine the amount of recombinant antibody produced/cell/day. These cells produce extremely high levels of recombinant antibody ranging from 14 to 43 pg/cell/day. This level of productivity was equal to or higher than the amount of recombinant antibody produced by the original D12 cell line.

To determine if the three fold variation in the specific productivity of recombinant antibody in these cells is due to differences in RNA levels or clonal variation, selected cell lines were plated and specific productivity was measured and RNA was isolated from the same original cell pool. Northern analysis was performed on the isolated RNA using immunoglobulin heavy and light chain constant region genes as hybridization probes. The amount of RNA loaded per lane was normalized to murine beta actin expression and the strength of the hybridization signal was quantitated. The results of this experiment indicate that the amount of RNA is relatively constant from cell line to cell line. This suggests that the variation in antibody expression in these cells is due to cellular factors and not primarily caused by different RNA levels.

The following Examples are provided as illustrative of the present invention without, however, limiting the same thereto.

EXAMPLE 1

Library Construction

A cell line was generated by electroporating a Sal I linearized p9014 [Palladino et al., 1993, Biotechniques, 14, pp. 754–755] into the murine plasmacytoma cell line NS/O and selecting for stable integrants by growth in glutamine free media [DeMartino et al. Antibody, Immunoconjugates and Radiophannaceuticals 1991 4:829–835 and Singer et. al. Journal of Immunology 1993 150:2844–2857]. From the clones generated, cell line D12 was shown to express recombinant antibody at exceptionally high levels (>15 pg/cell/day). The high specific productivity of this clone suggests that the p9014 vector had inserted into the mouse genome at a privileged site for expression. To clone the 5' genomic DNA/plasmid junction, a genomic library was constructed using Lambda-Gem 11 Xho I Half-Site Arms Cloning System (Promega) following the manufacturer's protocol. D12 genomic DNA was partially digested with Mbo I (Boehringer-Mannheim). Positive plaques were identified using two different probes: 1) Xmn I/Pst I fragment of the ampicillin resistance gene (354 bp) and 2) a 300 bp fragment of exon 7 of hamster glutamine synthetase gene.

To clone the 3' plasmid/genomic DNA junction, a genomic library was constructed using Lambda/Zap II/Gigapack II Gold cloning kit (Stratagene). Both vector and D12 genomic DNA were digested to completion with Xba I (Boehringer-Mannheim), the products were ligated (Ligation Kit, Stratagene), and packaged following the manufacturer's protocols. Positive plaques were identified using the human kappa constant region gene as probe. All probes were labeled by nick translation. Phage DNA was isolated using LambdaSorb (Promega) following the manufacturer's protocol.

Phage inserts were subcloned into pSP72 vector (Promega). Plasmid DNA from bacteria was isolated using the standard alkaline lysis method. Inserts were sequenced by the Sanger dideoxy chain termination method.

EXAMPLE 2
Isolation of the Germline Murine IgG2A Gene from NS/O Cells

An MboI partial digest of DNA isolated from the murine plasmacytoma cell line NS/0 was inserted into Promega's Lambda Gem-11 vector and $1.8 \times 10^6$ independent plaques were screened with a probe (BglII-BstX1) derived from the $IgG_{2A}$ M2 3' untranslated region. Fourteen positive bacteriophage were plaque purified and large scale lysates were prepared. The recombinant bacteriophage were characterized by restriction mapping and Southern hybridization and one clone encompassing all of the coding region of the murine Ig gamma 2A gene was identified. A 5.1 kb BamHI fragment containing all of the IgG2A coding region (except the most 5' part of the CH1 exon), membrane exons and 3' untranslated region was excised and cloned into the BamHI site of a modified form of Bluescript (Stratagene) in which the SalI site of the multicloning site had been destroyed.

EXAMPLE 3
Construction of the IgG2A Targeting Plasmid

The plasmid containing 5.1 kb of the murine IgG2A gene was partially digested with StuI and linearized plasmid was gel purified. A unique SalI site was introduced into the IgG2A fragment by linker ligation and a subclone containing the added SalI site 39 b.p. upstream of the IgG2A M2 exon was selected. The modified 5.1 kb IgG2A insert was excised by digestion with BamHI, blunted with T4 DNA Polymerase, and cloned into the similarly blunted SalI site of the Ig expression vector. The final pIgG2A targeting plasmid was linearized for electroporation by digestion with SalI. A map of the final targeting plasmid is shown in FIG. 3.

EXAMPLE 4
Electroporations

NS/O cells were grown in Iscove's Modified Dulbecco's Medium (Sigma) supplemented with 10% Fetal Calf Serum and 4 mM Glutamine. 10 million cells were mixed with 25 µg of linearized pIgG2A in a volume of 800 µl phosphate buffered saline and electroporated using a Bio-Rad Gene Pulser (1.5 kV; 3 µF; electrode distance, 0.4 cm). Transfected cells were plated in Iscove's with 10% FCS and 1 mM Glutamine for GS selected clones. Selective medium (GS selection-Glutamine-free Iscove's, 10% dialyzed FCS, 1×Nucleosides, 1×Asparagine) was added to the wells 24 hours later. 147 wells were positive for cell growth and were assayed by ELISA.

EXAMPLE 5
ELISA

Screening of clones for recombinant antibody production was accomplished by ELISA (enzyme-linked immunosorbent assay). Culture supernatants from clones were diluted 1:10 and 1:100 in 1% BSA in PBS. The samples were added to 96-well microtiter plates (Immulon 2, Dynatech Laboratories, Inc.) coated with mouse monoclonal antibody to human lambda light chain (Zymed) and incubated at 37° C. for one hour. Mouse monoclonal anti-human IgG1 antibody conjugated to horseradish peroxidase (Zymed) was then added and incubated for one hour at 37° C. The plate was washed three times with PBS after each incubation. Detection of bound antibody was visualized by adding the substrate ABTS (2,2-azino-di(3-ethylbenzthiazoline) sulfonic acid) (Zymed). The color was allowed to develop for twenty minutes at room temperature. Absorbance was measured at 415 nm (BioRad Microplate Reader 3550) and antibody concentration calculated using Microplate Manager (BioRad) data analysis software. A standard curve was generated using two-fold serial dilutions of the recombinant antibody.

EXAMPLE 6
Identifying Homologous Recombinants by Southern Blotting

Genomic DNA from clones was isolated either by a proteinase K/SDS method or a rapid guanidine hydrochloride method (Maniatis, T., Fritsch, E. F., Sambrook, J. in Molecular Cloning: A Laboratory Manuel (Cold Spring Harbor Laboratory, Cold Spring Harbor, N.Y., 1982)).

To identify homologous recombinants, 10 µg of genomic DNA from high expressing clones, as well as non-producing control clones, was digested to completion with Hpa I, run on an 0.8% agarose gel, and transferred to nitrocellulose by the Southern method (Southern, E. J. Mol. Biol. 1975 98:503). The blots were hybridized with two different probes, 1) a~3.5 kb Xba I fragment downstream of the murine IgG2a locus, and 2) a SalI/BamHI fragment (276 bp) of pBR322 plasmid backbone. DNA probes for hybridization were labeled by nick translation (Rigby, P. J. J. Molec. Biol. 1977 113:237–251). Twenty wells expressing high levels of antibody were identified. Upon rescreening after clonal expansion, 12 of the 20 wells continued to produce high levels of antibody, all of which homologously recombined the expression vector into the genomic DNA.

EXAMPLE 7
Specific Productivity

Specific productivity of the clones were determined by plating the cells at a density of $3 \times 10^5$ cells/well in triplicate, in a 6-well tissue culture plate. The medium was collected from one well at 24 hours, the second well at 48 hours, and the third well at 72 hours. Cell counts were taken at each time point. The medium was analyzed for recombinant antibody concentration using a POROS protein A affinity column. Specific productivity, expressed as picogram/cell/day, was calculated using the Kalaidagraph program. The levels of antibody production ranged between approximately 14 to approximately 43 pg/cell/day.

EXAMPLE 8
RNA Analysis

For each cell line, $10^8$ cells were washed three times with 1xPBS, lysed in 4M guanidine isothiocyanate and disrupted using a tissue homogenizer. The lysate was layered onto a 5.7 M CsCl cushion and spun overnight in an SW28 rotor at 20,000 rpm at 20° C. The RNA was recovered by dissolving the pellet in $dH_2O$ followed by an ethanol precipitation. Concentration of RNA was determined by reading the optical density at a wavelength of 260 nm.

10 μg of total RNA was run for each cell line on a formaldehyde/agarose gel in 1xMOPS buffer for three hours at 180V and then transferred to nitrocellulose paper essentially as described (Chirgwin et. al. Biochem. 18: 5294–5299 [1979]).

The RNA blots were hybridized to the following $^{32}$P-labeled mouse DNA probes: a.) 2 kb EcoR1-Xho1 fragment which contains the human IgG1 constant region; b.) 600 bp EcoR1-Xba1 fragment which contain the human Iglambda C2 constant region; c.) 1200 bp EcoR1-BamHI fragment from the mouse beta-actin gene which was generated through RT-PCR amplification using the oligonucleotides 5'-CUA CUA CUA CUA ATG GAT GAC GAT ATC GCT GC-3' (SEQ.ID.NO.:1) and 5' CAU CAU CAU CAU ACG CAG CTC AGT AAC AGT CC-3' (SEQ.ID.NO.:2). One RNA blot was hybridized with each of the two immunoglobulin probes overnight at 42° C. in 10% dextran sulfate, 4xSSC, 40% formamide, 0.8% Denhardt's Tris buffered solution. After hybridization filters were washed with 2xSSC, 0.1% SDS three times at room temperature and with 0.1xSSC, 0.1% SDS two times for twenty minutes at 50° C. before autoradiography. Signal intensity was determined on a Phosphorimager. After quantitation with the two immunoglobulin probes, the filters were stripped of signal by washing at 70° C. for 15 minutes in $dH_2O$ and rehybridized with the beta-actin probe to permit normalization for the amount of RNA loaded in each lane. Each of the cell lines produced approximately equivalent amounts of antibody-specific RNA.

EXAMPLE 9
Transfection of NS/O Cells

NS/O cells were maintained in exponential growth in the following medium: Iscove's Minimum essential medium supplemented with 10% heat inactivated Fetal Bovine Serum and 4 mM Glutamine; they were maintained at 37° C. in a humidified incubator set at 5% to 6.5% $CO_2$.

The plasmid for transfection was linearized by digestion with a restriction enzyme at a unique site; the preferred unique site was one situated outside the foreign gene expression sequences, in the bacterial sequences of the vector. After restriction, DNA was deproteinized by phenol extraction, phenol/chloroform (1:1) extraction and one final extraction with chloroform; it was then precipitated under sterile conditions in a biological safety cabinet, using a final concentration of 0.2–0.4 M sodium chloride and 70% ethanol. DNA was resuspended in sterile distilled water at a calculated 1 mg/1 ml concentration. DNA was either used immediately or frozen (–20° C.) until use.

On the day of transfection, viable cell counts were taken for the stock NS/0 culture. A total of $1\times10^7$ viable cells were used per transfection cuvette. The cells were first collected by centrifugation at 3,000xg for 5 minutes at room temperature; pelleted cells were then washed twice with sterile phosphate buffered saline (PBS) and resuspended in PBS at a concentration of $10^7$ cells per 800 mls. The cell suspension was maintained on ice from this point on. $10^7$ cells were transferred gently to a 0.4 cm (distance between electrodes) BioRad cuvette, under sterile conditions in a biological safety cabinet. 40 mg of linearized plasmid DNA in solution was mixed with the cells gently and the cuvette was kept on ice for 5 minutes. Before electroporation, the outside of the cuvette was wiped dry, then placed in the cuvette holder of a "BioRad Gene Pulser". The gene pulser was set to deliver 3 mF at 1500 volts per pulse. Two consecutive pulses were used. The cuvette was then placed on ice for 2–5 minutes and then the cells were transferred to 30 ml of modified growth medium containing 1 mM glutamine, rather than 4 mM glutamine, in a 50 ml disposable sterile tube. 10 ml of cell suspension out of 30 ml was distributed into one 96 well microtiter dish, approximately 100 ml per well; 10 ml of cell suspension, (from the remaining 20 ml) was diluted with 10 ml of modified growth medium and distributed to two 96 well microtiter dishes, approximately 100 ml per well; the final 10 ml of cell suspension was diluted with 30 ml of modified growth medium and distributed over four 96-well microtiter dishes at approximately 100 ml per well. These plates were incubated overnight in a humidified incubator set at 37° C. with 5%–6.5% $CO_2$.

Selective Medium:

Selective medium for GS selection was as follows:

Iscove's Minimum Essential Medium (Glutamine-free; Sigma)
10% Dialyzed Fetal Bovine Serum (from Hyclone)
1xNucleosides*
1xAsparagine**
50xRibonucleosides Stock Solution:
  35 mg adenosine
  35 mg guanosine
  35 mg cytidine
  12 mg thymidine
(each from Sigma, cell culture grade) Make up to 100 ml with sterile distilled water. Filter sterilize through 0.1 m filter unit and store frozen (–20° C.) in 10 ml aliquots.
**100xAsparagine: 600 mg per 100 ml of sterile distilled water, filter sterilize through an 0.1 m filter unit and store at 4° C.

Selection:

24 hours post transfection each 96 well microtiter dish was fed with 100 μl of selective medium and incubated in a humidified incubator set at 37° C. with 5% to 6.5% $CO_2$ until colonies came up, which took approximately 3 to 3.5 weeks. No feeding was required unless wells begin to dry out; plates were monitored at 3–4 day intervals. The wells with colonies growing eventually turned yellow and at this point those wells were assayed by removing 50 to 100 μl of culture fluid and refeeding the wells with selective medium (to maintain viable clones).

What is claimed is:

1. A homologous recombination insertional expression vector capable of expressing a recombinant gene in a NS/O cell, said vector comprising said recombinant gene and gamma 2A locus-specific DNA sequences capable of homologous recombination targeting into the NS/O gamma 2A locus, wherein said recombinant gene comprises a nucleic acid sequence encoding for a recombinant protein and a promoter transcriptionally coupled to said nucleic acid sequence, wherein said promoter is capable of providing for expression in said NS/O cell and said recombinant gene is capable of expression in said NS/O cell.

2. The vector of claim 1, wherein said vector further comprises a transcription unit encoding a selectable marker.

3. The vector of claim 2, wherein said vector further comprises an origin of replication for autonomous replication in a host cell.

4. The vector of claim 2, wherein said recombinant protein is a human immunoglobulin heavy chain.

5. The vector of claim 2, wherein said selectable marker is selected from the group consisting of xanthine-guanine phosphoribosyltransferase and dihydrofolate reductase.

6. The vector of claim 2, wherein said promoter is the human cytomegalovirus immediate early promoter.

7. The vector of claim 6, wherein said selectable marker is glutamine synthetase.

8. The vector of claim 3, wherein said selectable marker is selected from the group consisting of xanthine-guanine phosphoribosyltransferase and dihydrofolate reductase.

9. The vector of claim 3, wherein said recombinant protein is a human immunoglobulin heavy chain.

10. The vector of claim 9, wherein said promoter is the human cytomegalovirus immediate early promoter.

11. The vector of claim 10 wherein said selectable marker is glutamine synthetase.

12. The vector of claim 4, wherein said selectable marker is selected from the group consisting of xanthine-guanine phosphoribosyltransferase and dihydrofolate reductase.

13. The vector of claim 6, wherein said promoter is the human cytomegalovirus immediate early promoter.

14. The vector of claim 1, wherein said vector further comprises an origin of replication for autonomous replication in a cell.

15. The vector of claim 14, wherein said recombinant protein is a human immunoglobulin heavy chain.

16. The vector of claim 15, wherein said vector further comprises a recombinant gene encoding a human light chain immunoglobulin.

17. The vector of claim 16, wherein said vector further comprises a selectable marker.

18. The vector of claim 17, wherein said selectable marker is glutamine synthetase.

19. The vector of claim 18, wherein said promoter is the human cytomegalovirus intermediate early promoter.

* * * * *

SEQUENCE LISTING

<160> NUMBER OF SEQ ID NOS: 2

<210> SEQ ID NO 1
<211> LENGTH: 32
<212> TYPE: DNA
<213> ORGANISM: Artificial Sequence
<220> FEATURE:
<223> OTHER INFORMATION: Amplification oligonucleotide
      Bases 1-12 RNA

<400> SEQUENCE: 1
cuacuacuac uaatggatga cgatatcgct gc                          32

<210> SEQ ID NO 2
<211> LENGTH: 32
<212> TYPE: DNA
<213> ORGANISM: Artificial Sequence
<220> FEATURE:
<223> OTHER INFORMATION: Amplification oligonucleotide
      Bases 1-12 RNA

<400> SEQUENCE: 2
caucaucauc auacgcagct cagtaacagt cc                          32